United States Patent [19]

Suzuki

[11] 4,129,595
[45] Dec. 12, 1978

[54] PREPARATION OF CHLOROACETYL CHLORIDE

[75] Inventor: Shigeto Suzuki, San Francisco, Calif.

[73] Assignee: Chevron Research Company, San Francisco, Calif.

[21] Appl. No.: 891,429

[22] Filed: Mar. 29, 1978

[51] Int. Cl.$^2$ .............................................. C07C 51/58
[52] U.S. Cl. ................................................. 260/544 Y
[58] Field of Search .................................... 260/544 Y

[56] References Cited
PUBLICATIONS

E. E. Blaise et al., Comptes Rendus (France), vol. 174, pp. 1173–1174, (1922), (Chem. Abstr., vol. 16, 2480).

Primary Examiner—Gerald A. Schwartz
Attorney, Agent, or Firm—D. A. Newell; John Stoner, Jr.

[57] ABSTRACT

Chloroacetyl chloride is prepared by reacting glycolic acid with thionyl chloride in the presence of nitrogen-containing organic compound or phosphine compound.

3 Claims, No Drawings

PREPARATION OF CHLOROACETYL CHLORIDE

BACKGROUND OF THE INVENTION

1. Field of the Invention

The present invention relates to the preparation of chloroacetyl chloride. More particularly, the invention relates to the preparation of chloroacetyl chloride by reacting glycolic acid with thionyl chloride in the presence of nitrogen-containing organic compound or phosphine compound.

2. Description of the Prior Art

*Comptes Rendus,* Volume 152, page 1601, dated June 6, 1911, shows the preparation of alkyl chloride by the reaction of alcohol and thionyl chloride in the presence of a molar amount of pyridine as acid acceptor.

*Comptes Rendus,* Volume 174, page 1173, dated May 1, 1922, shows the production of chloroacetyl glycolyl chloride by reaction of glycolic acid and thionyl chloride.

*Survey of Organic Synthesis* by Buehler and Pearson, pages 860 and 861, published 1970 by Wiley-Interscience, New York, shows the production of acyl chlorides by reaction of the acid and thionyl chloride employed with iodine or with a trace of pyridine.

U.S. Pat. No. 2,848,491 shows the preparation of carboxylic acid chlorides by reaction of the acid with phosgene in the presence of nitrogen-containing compounds and mentions the preparation of chloroacetyl chloride from chloroacetic acid.

U.S. Pat. No. 3,418,365 shows the preparation of beta-chloropropionyl chloride by the reaction of beta-propiolactone with thionyl chloride.

U.S. Pat. No. 3,758,659 shows the preparation of chloroacetyl chloride by reaction of ketene with chlorine in the presence of alpha-butyl-gamma-butyrolactone.

U.S. Pat. No. 3,880,923 shows the preparation of mono-chloroacetyl chloride by reaction of acetyl chloride and chlorine in sulfuric acid.

U.S. Pat. No. 3,883,589 shows the preparation of chloroacetyl chloride by reaction of ketene and chlorine in the presence of a tertiary phosphate ester such as tris(2-chloroethyl) phosphate.

SUMMARY OF THE INVENTION

In accordance with the present invention, a process is provided for preparing chloroacetyl chloride which comprises reacting glycolic acid with thionyl chloride in the presence of a catalytic amount of a nitrogen-containing hydrocarbyl organic compound having a total of not more than about 10 carbon atoms or hydrocarbyl phosphine compound having a total of not more than about 30 carbon atoms, maintaining the reaction at a temperature and for a time sufficient to convert the glycolic acid to chloroacetyl chloride, and separating chloroacetyl chloride.

Typical alcohols and carboxylic acids when heated with thionyl chloride with or without a basic nitrogen-containing organic compound such as pyridine as acid acceptor in stoichiometric amounts will give, respectively, the corresponding alkyl chlorides and acyl chlorides. By way of contrast, glycolic acid, which has both an alcohol hydroxyl group and an acid carboxylic group, when heated with thionyl chloride gives complex mixtures of products, none of which being chloroacetyl chloride. Accordingly, it was not expected that chloroacetyl chloride would be obtained by reaction of glycolic acid with thionyl chloride in the presence of a catalytic amount of nitrogen-containing hydrocarbyl organic compound or hydrocarbyl phosphine compound at high conversion and yield in accordance with the present invention.

DETAILED DESCRIPTION OF THE INVENTION

The nitrogen-containing hydrocarbyl organic compounds or hydrocarbyl phosphine compounds which provide the catalyst in accordance with the present invention are characterized primarily by hydrocarbyl groups which have a total of not more than 10 carbon atoms in the case of the nitrogen-containing hydrocarbyl organic compounds or not more than 30 carbon atoms in the case of the hydrocarbyl phosphine compounds. Although for present purposes hydrocarbyl groups are preferred, there may be substituents which are known to be chemically inert to the glycolic acid and thionyl chloride reactants.

The nitrogen-containing hydrocarbyl organic compound catalysts in accordance with the present invention include amides, imides, amines, quaternary ammonium salts and ureas. The preferred catalysts are the N,N-disubstituted amides such as N,N-dimethyl formamide, N-methylpyrrolidone, etc., the N-monosubstituted amides such as N-methyl formamide, N-methyl acetamide, etc., the tertiary amines such as pyridine, triethylamine, etc., secondary amines such as pyrrolidine, diethylamine, etc., and substituted ureas such as tetramethyl urea.

The hydrocarbyl phosphine compound catalysts in accordance with the present invention include trihydrocarbyl phosphines and phosphine oxides having the formula

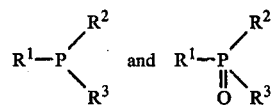

in which $R^1$, $R^2$ and $R^3$ are hydrocarbyl groups which may be the same or different and contain a total of not more than about 30 carbon atoms. Included are tributylphospine, triphenylphosphine, dibutyl-n-phenylphosphine, and tri-n-octylphosphine oxide.

The proportion of the catalytic nitrogen-containing hydrocarbyl organic compound or hydrocarbyl phosphine compound in accordance with the present invention is found to be critical and must be kept low in the range of amounts sufficient to provide the catalytic reaction of glycolic acid and thionyl chloride. For present purposes the catalyst should be in amounts not more than about 0.15 mols per mol of glycolic acid and preferably in the range of 0.001 to 0.1 mols per mol of glycolic acid. By way of contrast, when the basic nitrogen-containing hydrocarbyl organic compounds are prepared in approximately molar amounts as acid acceptors, it is found that the reaction is completely inhibited and no chloroacetyl chloride is obtained.

The glycolic acid is reacted with thionyl chloride in stoichiometric amounts. Thus, one mol of glycolic acid is reacted with 2 mols of thionyl chloride. Excess thionyl chloride may be employed if desired.

The temperatures of the reaction of glycolic acid and thionyl chloride are over a wide range. An advantage of the process lies in the employment of moderate temperatures which minimize the need for heating and cooling during the reaction. For present purposes temperatures in the range of from about 20 to about 100° C. are preferred.

The times required for reaction of glycolic acid and thionyl chloride will vary over a wide range, in general with the higher temperatures providing shorter reaction times and lower temperatures providing longer reaction times. At about 100° C. the reaction is substantially complete in about 30 minutes, while at room temperature a longer time of about 60 minutes may be required.

The reaction of glycolic acid and thionyl chloride in accordance with the present invention is conveniently carried out by contacting the reactants and the catalyst in the liquid phase. If desired, inert solvents may be employed to facilitate handling of reactants. Suitable solvents include acetyl chloride, 1,2-dichloroethane, chlorobenzenes, benzene, hexane, and the like. The chloroacetyl chloride product of the reaction is readily separated from the reaction mixture by conventional means, as for example by distillation.

EXAMPLES

The process of the present invention is illustrated by the following examples. Unless otherwise specified, the proportions in the examples are on a weight basis.

EXAMPLE 1

A 100-ml, 3-necked round-bottom flask, equipped with a magnetic stirrer, a condenser, and a thermometer, was charged with 2.9 grams (0.04 mol) of dimethyl formamide and 36 grams (0.30 mol) of thionyl chloride. This solution was stirred at room temperature and 7.6 grams (0.1 mol) of glycolic acid was added in small increments over a period of 5 minutes. Then the resulting reaction mixture was stirred at room temperature for 18 hours. At the end of this time, an aliquot was analyzed by NMR. This analysis showed greater than 99% conversion of glycolic acid and a 98% yield of chloroacetyl chloride. The remainder of the reaction mixture was distilled in a vacuum still at 100 mm Hg to give 9.5 grams (84%) of chloroacetyl chloride having a boiling point in the range of 46° to 50° C.

Other preparations were carried out by a similar procedure. The composition of the reaction mixture and the results are given in Table I.

TABLE I

PREPARATION OF CHLOROACETYL CHLORIDE

| Ex. No.[1] | Additive | (moles) | Glycolic Acid (moles) | Thionyl Chloride (moles) | Time (hrs) | Temp. (°C) | Conversion of Acid (%) | Yield of Chloroacetylchloride (mole %) |
|---|---|---|---|---|---|---|---|---|
| 2 | none | — | 0.1 | 0.3 | 2.5 | 80 | >99 | none |
| 3[2] | none | — | 0.1 | 0.3 | 24 | 22 | >99 | none |
|  |  | — | — | 0.3 | 48 | 22 | — | none |
|  | 10.5 grams ZnCl$_2$ | — | — | — | 2 | 180 | — | trace |
|  |  | — | — | — | 1 | 194 | — | trace |
| 4 | pyridine | 0.2 | 0.1 | 0.2 | 1 | 105 | >99 | none |
| 5 | pyridine | 0.01 | 0.1 | 0.3 | 2 | 22 | — | <1 |
|  |  | — | — | — | 2 | 80 | — | >95 |
| 6 | dimethylformamide | 0.04 | 0.1 | 0.3 | 1 | 22 | — | <1 |
|  |  | — | — | — | 3 | 22 | — | 12 |
|  |  | — | — | — | 65 | 22 | — | 50 |
|  |  | — | — | — | 90 | 22 | — | >98 |
| 7[3] | dimethylformamide | 0.04 | 0.1 | 0.3 | 1 | 22 | — | <1 |
|  |  | — | — | — | 3 | 22 | — | 3 |
|  |  | — | — | — | 1 | 80 | — | >98 |
| 8 | dimethylformamide | 0.013 | 0.1 | 0.3 | 2 | 22 | — | <1 |
|  |  | — | — | — | 90 | 22 | — | >95 |
| 9 | dimethylformamide | 0.005 | 0.1 | 0.3 | 2 | 80 | — | >95 |
|  |  | — | — | — | 5 | 80 | — | no change |
| 10 | dimethylformamide | 0.04 | 0.1 | 0.22 | 2 | 80 | — | 60 |
|  |  | — | — | — | 5 | 80 | — | 70 |
| 11 | none | — | 0.1 | 0.3 | 2 | 80 | — | <1 |
|  | dimethylformamide | 0.01 | — | — | 2 | 80 | — | 53 |
| 12 | dimethylacetamide | 0.01 | 0.1 | 0.3 | 2 | 22 | — | <1 |
|  |  | — | — | — | 2 | 80 | — | >95 |
| 13 | N-methylpyrrolidone | 0.01 | 0.1 | 0.3 | 2 | 22 | — | <1 |
|  |  | — | — | — | 2 | 80 | — | >95 |
| 14 | acetamide | 0.01 | 0.1 | 0.3 | 2 | 22 | — | <1 |
|  |  | — | — | — | 2 | 80 | — | 17 |
| 15 | formamide | 0.01 | 0.1 | 0.3 | 2 | 22 | — | <1 |
|  |  | — | — | — | 2 | 80 | — | 8 |
| 16 | N-methylformamide | 0.1 | 0.1 | 0.3 | 2 | 22 | — | 13 |
|  |  | — | — | — | 2 | 80 | — | 59 |
| 17 | N-methylformamide | 0.01 | 0.1 | 0.3 | 2 | 22 | — | <1 |
|  |  | — | — | — | 2 | 80 | — | 95 |
| 18 | N-methylacetamide | 0.1 | 0.1 | 0.3 | 2 | 22 | — | 9 |
|  |  | — | — | — | 2 | 80 | — | 78 |
| 19 | N-methylacetamide | 0.01 | 0.1 | 0.3 | 2 | 22 | — | <1 |
|  |  | — | — | — | 2 | 80 | — | >95 |
| 20 | 2-pyrrolidone | 0.1 | 0.1 | 0.3 | 2 | 22 | — | 17 |
|  |  | — | — | — | 2 | 80 | — | 41 |
| 21 | 2-pyrrolidone | 0.1 | 0.1 | 0.3 | 2 | 22 | — | <1 |
|  |  | — | — | — | 2 | 80 | — | 82 |
| 22 | triethylamine | 0.01 | 0.1 | 0.3 | 2 | 22 | — | <1 |
|  |  | — | — | — | 2 | 80 | — | >95 |
| 23 | pyrrolidine | 0.01 | 0.1 | 0.3 | 2 | 22 | — | <1 |
|  |  | — | — | — | 2 | 80 | — | >95 |
| 24 | n-butylamine | 0.01 | 0.1 | 0.3 | 2 | 22 | — | <1 |
|  |  | — | — | — | 2 | 80 | — | 94 |
| 25 | succinimide | 0.01 | 0.1 | 0.3 | 2 | 22 | — | <1 |
|  |  | — | — | — | 2 | 80 | — | 9 |
| 26 | tetramethylurea | 0.01 | 0.1 | 0.3 | 2 | 22 | — | <1 |

TABLE I-continued
PREPARATION OF CHLOROACETYL CHLORIDE

| Ex. No.[1] | Additive | Glycolic Acid (moles) | Thionyl Chloride (moles) | Time (hrs) | Temp. (°C) | Conversion of Acid (%) | Yield of Chloroacetylchloride (mole %) |
|---|---|---|---|---|---|---|---|
| | | | | 2 | 80 | — | >95 |
| 27 | urea | 0.01 | 0.1 | 0.3 | 2 | 22 | — | < 1 |
| | | — | — | — | 2 | 80 | — | 48 |
| 28 | tetramethyl ammonium acetate | 0.01 | 0.1 | 0.3 | 2 | 22 | — | < 1 |
| | | — | — | — | 2 | 80 | — | 83 |
| 29 | tributylphosphine | 0.01 | 0.1 | 0.3 | 2 | 22 | — | 20 |
| | | — | — | — | 2 | 80 | — | >95 |
| 30 | tri-n-octylphosphine oxide | 0.005 | 0.1 | 0.3 | 2 | 22 | — | < 1 |
| | | — | — | — | 2 | 80 | — | >95 |
| 31 | none | — | 0.1 | 0.3 | 2 | 22 | — | < 1 |
| | | — | — | — | 2 | 80 | — | 2 |

Footnotes
[1] Those examples having two or more time entries were carried out continuously with just an aliquot removed for analysis
[2] After 24 hours, 0.3 moles of extra thionyl chloride was added; after 48 more hours, zinc chloride was added.
[3] A solution of glycolic acid in dimethylformamide was added to thionyl chloride.

While the character of this invention has been described in detail with illustrative examples, this has been done by way of illustration only and without limitation of the invention. It will be apparent to those skilled in the art that modifications and variations of the illustrative examples may be made in the practice of the invention within the scope of the following claims.

What is claimed is:

1. A process for preparing chloroacetyl chloride which comprises reacting glycolic acid with 2 moles of thionyl chloride in the presence of a catalytic amont of a nitrogen-containing hydrocarbyl organic compound having a total of not more than about 10 carbon atoms selcted from the group consisting of amides, imides, amines, quaternary ammonium salts and ureas or a hydrocarbyl phosphine compound having a total of not more than about 30 carbon atoms selected from the group consisting of trihydrocarbylphosphines and trihydrocarbylphosphine oxides, wherein not more than 0.15 moles of the catalyst is used per mole of glycolic acid, maintaining the reaction at a temperature and for a time sufficient to convert the glycolic acid to chloroacetyl chloride, and separating chloroacetyl chloride.

2. A process according to claim 1 wherein the catalyst is N,N-disubstituted amide or N-monosubstituted amide.

3. A process according to claim 1 wherein the catalyst is tributylphosphine or tri-n-octylphosphine oxide.

* * * * *